(12) United States Patent
Trabucco et al.

(10) Patent No.: US 8,623,096 B2
(45) Date of Patent: Jan. 7, 2014

(54) DOUBLE LAYER SURGICAL PROSTHESIS TO REPAIR SOFT TISSUE

(75) Inventors: Ermanno E. Trabucco, Muttontown, NY (US); Margherita Bosio, Turin (IT); Pier Aldo Crepaldi, Vercelli (IT); Roberta Lamberti, Ulzio (IT)

(73) Assignee: Herniamesh s.r.l., Chivasso (IT)

( * ) Notice: Subject to any disclaimer, the term of this patent is extended or adjusted under 35 U.S.C. 154(b) by 762 days.

(21) Appl. No.: 12/434,209

(22) Filed: May 1, 2009

(65) Prior Publication Data

US 2009/0276057 A1    Nov. 5, 2009

(30) Foreign Application Priority Data

May 2, 2008   (IT) ................ TO2008A0329

(51) Int. Cl.
*A61F 2/02*         (2006.01)
(52) U.S. Cl.
USPC ........................................... 623/23.72
(58) Field of Classification Search
USPC ........... 623/23.72, 23.74; 606/151, 154, 155; 600/37
See application file for complete search history.

(56) References Cited

U.S. PATENT DOCUMENTS

| | | | |
|---|---|---|---|
| 5,593,441 A | | 1/1997 | Lichtenstein |
| 5,766,246 A | * | 6/1998 | Mulhauser et al. ........... 606/151 |
| 5,922,026 A | * | 7/1999 | Chin ........................... 623/23.72 |
| 6,270,530 B1 | | 8/2001 | Eldridge et al. |
| 2002/0133236 A1 | | 9/2002 | Rousseau |
| 2006/0282103 A1 | | 12/2006 | Fricke |

FOREIGN PATENT DOCUMENTS

| | | |
|---|---|---|
| EP | 1797842 | 6/2007 |
| EP | 1847233 | 10/2007 |
| WO | 2004096086 | 11/2004 |

OTHER PUBLICATIONS

Klinge et al., "Prosthetic Implants for Hernia Repair", BJS, vol. 90(12), pp. 1457-1458 (2003).
Klinge et al., "Modified mesh for hernia repair that is adapted to the physiology of the abdominal wall", Eur J Surg 164:951-960 (1998).

* cited by examiner

*Primary Examiner* — Thomas McEvoy
(74) *Attorney, Agent, or Firm* — Troutman Sanders LLP

(57) ABSTRACT

A prosthesis for the treatment of hernias and/or laparoceles via an intraperitoneal route, having a mesh of filaments of non-resorbable and biocompatible polymer material having interstices permitting tissue growth and a sheet of polymer material having barrier properties and low adhesion to sensitive organs and tissues. The sheet is superimposed upon and joined to the mesh so as to form a stratified structure. In particular, the sheet is joined to mesh through a plurality of filaments located alongside each other at a spacing of not more than 5 mm. Each filament has a plurality of attachment sites to the mesh which are not more than 15 mm apart, and each length of filament between two successive attachment sites projects from the surface of the mesh facing sheet and is fused to the sheet.

17 Claims, 2 Drawing Sheets

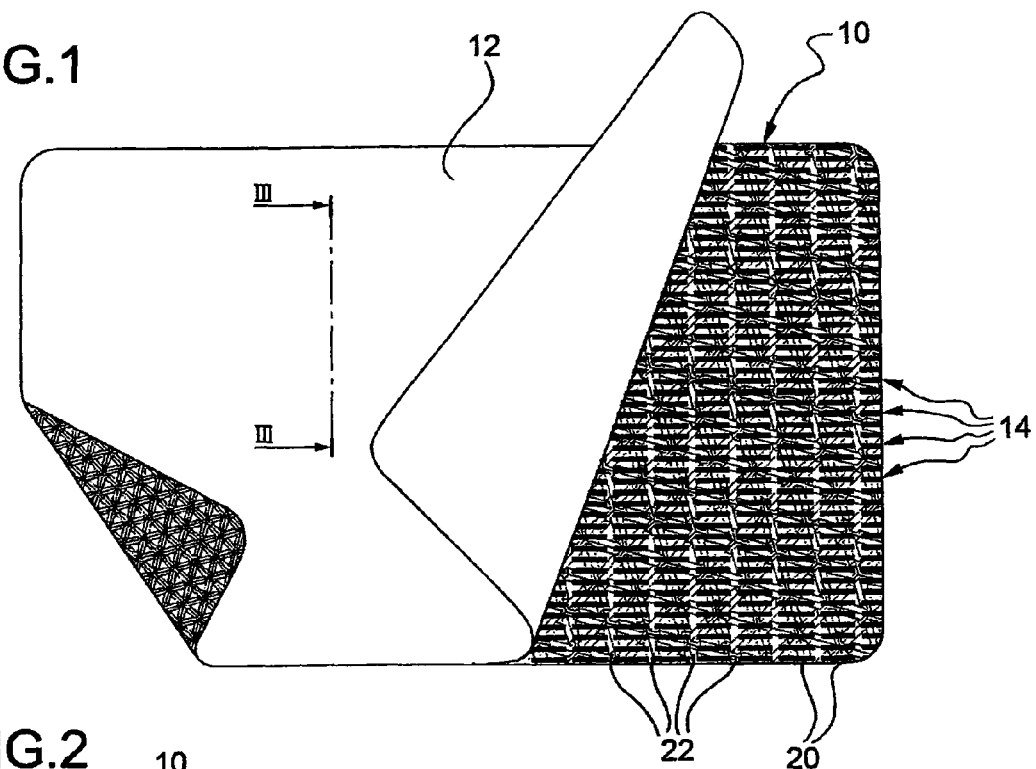
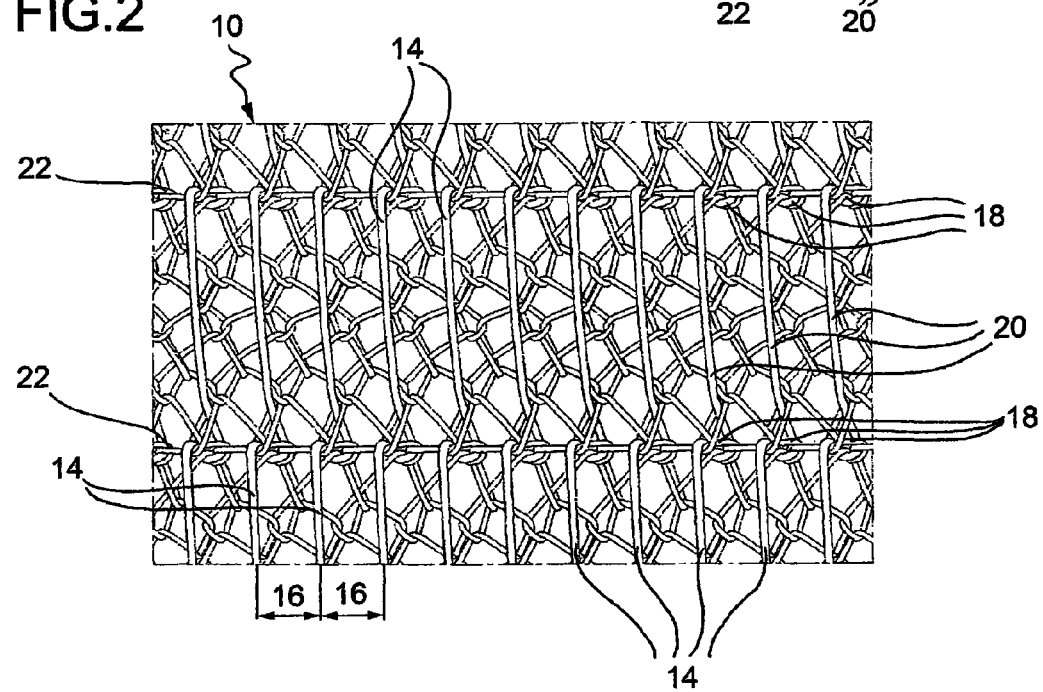

DOUBLE LAYER SURGICAL PROSTHESIS TO REPAIR SOFT TISSUE

CROSS REFERENCE TO RELATED APPLICATION

This application claims priority to Italian Application Serial No. TO2008A000329 filed May 2, 2008 under 35 U.S.C. §119. This application is incorporated by reference in its entirety.

FIELD OF THE INVENTION

This invention relates to a surgical prosthesis for the repair of soft tissues, in particular for the treatment of hernias and/or laparoceles, or defects of the abdominal wall, using an intraperitoneal route.

BACKGROUND OF THE INVENTION

A typical surgical prosthesis includes a mesh made of a non-resorbable and biocompatible polymer. The mesh is composed of filaments that have interstices which permit tissue growth. The prosthesis also includes a sheet of polymer material having barrier properties and low adhesion to sensitive organs and tissues. This sheet is superimposed upon and joined to the mesh to form a stratified structure.

The prosthesis is implanted in a patient so that the mesh is in contact with the patients abdominal wall to reinforce it and stimulate the fibroplastic response. The sheet forming the barrier layer is placed in contact with the viscera of the patient to minimize adhesions.

A known prosthesis of this type is described in U.S. Pat. No. 6,270,530 to Eldridge et al. According to this patent, the mesh is joined to the sheet through a further intermediate mesh which is sewn to the first mesh on one side and is fused to the barrier sheet on the other through heat and pressure.

The intermediate mesh renders the structure of this prosthesis rather thick, rigid and heavy. As a consequence it is difficult to wrap the mesh in order to introduce it into the abdominal cavity using a trocar (or an instrument which, after creating the pneumoperitoneum, makes it possible to pass surgical instruments through holes made in the abdominal wall), restricting the possibilities for location. In addition to this the large quantity of material present in this prosthesis conflicts with the "less is more" concept expressed by U. Klinge and V. Schumpelick, in "*Prosthetic Implants For Hernia Repair*" BJS, Vol. 90(12), December 2003:1457-1458. According to this concept, the quantity and quality of the inflammatory response directly correlates with the quantity of implanted prosthetic material and the surface area in contact with host tissue. In particular, this inflammatory response causes the formation of scar tissue which covers the mesh, rendering it rigid and causing discomfort and pain to the patient. This is a serious drawback of the prior art mesh.

The object of this invention is therefore to provide a prosthesis which is improved in comparison with those described in the prior art.

SUMMARY OF THE INVENTION

A prosthesis according to the invention joins a sheet to the mesh by a plurality of filaments located alongside each other. The filaments are spaced not more than 5 mm apart. Each filament has a plurality of sites of attachment to the mesh. The attachment points not more than 15 mm apart. Further, each length of filament between two successive attachment sites projects from the side of the mesh facing the sheet and is fused to the sheet.

In the prosthesis according to the invention the joining filaments act as spacers located between the mesh and the sheet. The joining filaments prevent damage to the mesh and/or the continuity of the barrier film during the process of fusing them with the sheet, and preventing the interstices in the mesh from being obstructed. Additionally the joining filaments have a mass and rigidity which is very much less than that of an intermediate mesh or other joining means, so that the ease of handling and flexibility of the prosthesis according to the invention are improved.

The structure of the joining filaments allows, at the time of implantation a number of benefits. A benefit of the present invention is that it allows the surgical prosthesis to be cut into the necessary shapes and dimensions for implantation without any damage and loss of fibres belonging to the mesh. The prosthesis of the present invention can be wrapped for insertion into the abdominal cavity using a trocar, and this eases extension at the anatomical implantation site.

Once implanted, the prosthesis of the present invention has values for resilience and strength such as to ensure a response which is compatible with normal physiological reactions and the anatomical and biomechanical dynamics of the abdominal wall without the mesh becoming separated from the sheet and/or the sheet being perforated by the mesh.

In one example, the thickness of the prosthesis according to the invention is between 0.4 and 0.6 mm, the weight per unit surface area is between 60 and 100 $g/m^2$ and the tensile strength is greater than the maximum intra-abdominal pressure measured using the principle of Pascal hydrostatics and equal to 16 N/cm, as specified by Klinge U., Klosterhalfen B., Conze J., et al in "*Modified mesh for hernia repair that is adapted to the physiology of the abdominal wall*", Eur J Surg 164:951-960, 1998.

As a whole, the prosthesis according to the invention has a lesser thickness which enables it to be implanted using a trocar, a device which also has small dimensions. The prosthesis also has reduced weight that helps in reducing the inflammatory reaction. A reduced inflammatory reaction reduces the rigidity in the abdominal wall, appreciably improving the patient's comfort and quality of life.

BRIEF DESCRIPTION OF THE DRAWINGS

Other advantages and characteristics of the present invention will become clear from the following detailed description which is given with reference to the appended drawings which are provided purely by way of non-limiting example and in which:

FIG. 1 is a partially exploded view of a prosthesis according to the invention;

FIG. 2 is a plan view on a magnified scale of a portion of the mesh forming part of the prosthesis in FIG. 1.

DETAILED DESCRIPTION OF THE INVENTION

Figure 3:
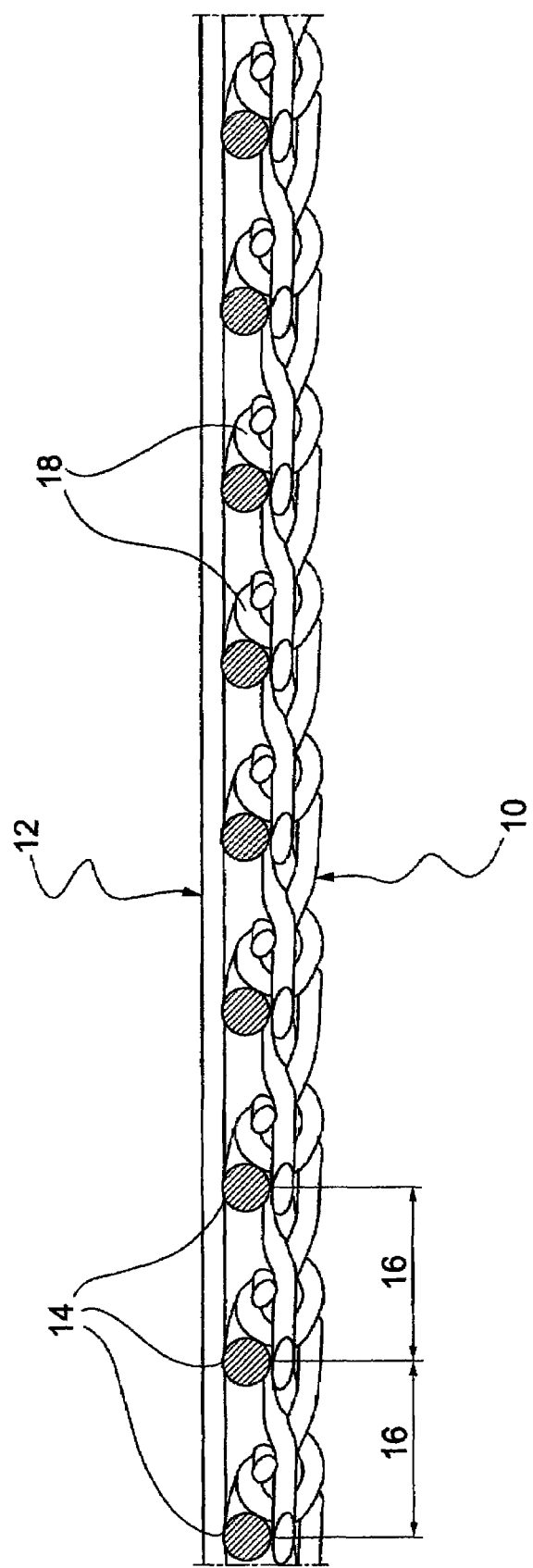
FIG. 3 is a view in cross-section on a magnified scale along the line III-III in FIG. 1.

FIG. 1 illustrates a surgical prosthesis for the repair of soft tissues, in particular for the treatment of hernias and/or laparoceles via an intraperitoneal route of the present invention A mesh 10 is made up of filaments of non-resorbable and biocompatible synthetic polymer material having interstices which permit tissue growth and a sheet 12 of polymer material having barrier properties and low adhesion to sensitive body organs and tissues. Sheet 12 is superimposed on mesh 10 and joined to it through a plurality of joining filaments 14 to form a stratified structure.

The material used for sheet 12 can be synthetic or natural, resorbable or not resorbable, for example expanded polytetrafluoroethylene, polyhuretane, collagen, polyglactin (PGLA), poly-l-lactide acid (PLLA), polydioxanone/poly-p-dioxanone (PDO or PDS), polycaprolacton or polyglecaprone. The material used for mesh 10, and for joining filaments 14, can be, for example, a monofilament polypropylene polyester, polyvinylidene fluoride (PVDF) or poly-tetrafluoroethene/poly-tetrafluoroethylene (PTFE).

As illustrated in FIGS. 2 and 3, joining filaments 14 are arranged side by side, and in an embodiment, substantially equally spaced. A spacing 16 between the filaments is less than or equal to 5 mm. In alternate embodiments, spacing 16 is not greater than 3 mm and another embodiment the spacing 16 is between 1 and 2 mm.

Each filament 14 has a plurality of attachment sites 18 to mesh 10 which are not more than 15 mm apart and, in another embodiment, not more than 10 mm apart the length 20 of filament 14 between two successive attachment sites 18 of the mesh 10 can vary from filament to filament or remain equal. In one preferred embodiment the lengths 20 of filament 14 are all equal and range between 5 mm and 9 mm. With this arrangement similar attachment sites 18 of various filaments 14 are arranged in rows 22 which are parallel to each other and substantially perpendicular to the adjacent lengths 20 of filaments 14.

Additionally, the diameter of joining filaments 14 is between about 160 and 200 μm greater than that of the filament in mesh 10, so, in an embodiment, the value of the ratio between these diameters lies between 1.1 and 2. The diameter of the joining filaments 14 is between 160 and 200 μm, while the diameter of the filament in mesh 10 is between 100 and 140 μm.

In addition to being attached to mesh 10, joining filaments 14 are fused to sheet 12 at projecting lengths 20 which act as bridges between successive attachment sites 18. Fusion is carried out using conventional procedures, for example through the combined action of heat and pressure in a hot rolling process. During the latter and subsequently when in use, joining filaments 14 keep mesh 10 at a distance from sheet 12, preventing the interstices which are essential to permit tissue growth from being obstructed, and preventing the filament in mesh 10 from perforating the sheet 12, interrupting its continuity. This process results in a cohesive prosthesis structure which is resistant to tearing and delamination, and is likewise resilient and flexible.

Further to the process, the sheet 12 is pulled from one set of rollers while mesh 10 is pulled from another. The sheet 12 and mesh 10 meet between two other rollers and are hot rolled at a temperature between about 350 and 410° F. and a pressure between about 5.7 and 8.5 psi. The materials are fed at about a rate of 15-50 inches per minute. As seen in FIG. 3, due to the three dimensional nature of the mesh 10, particularly joining filament 14, permits the mesh 10 to be bonded to the sheet 12 without it laying directly on one surface of the mesh 10. This forms a gap and prevents the sheet 12 from covering the openings formed between the filaments 14. This permits the mesh 10 to be integrated into the tissue it is in contact with and have the strength of sheet 12.

Naturally, the principle of the invention remaining the same, the forms of embodiment and details of construction may be varied widely with respect to those described and illustrated, which have been given purely by way of example, without thereby departing from the scope of the invention.

We claim:

1. A surgical prosthesis for the repair of soft tissues, in particular for the treatment of hernias and/or laparoceles via an intraperitoneal route, comprising:
   a mesh of spaced apart filaments of a non-resorbable and biocompatible polymer material having interstices which permit tissue growth;
   a sheet of polymer material having barrier properties and low adhesion to sensitive organs and tissues, the sheet superimposed upon and joined to the mesh so as to form a stratified structure;
   a plurality of second filaments located alongside each other with a spacing between said filaments less than or equal to 5 mm,
   wherein each filament of the plurality of second filaments has a plurality of attachment sites attaching the filament of the plurality of second filaments to the mesh, the attachment sites are spaced less than or equal to 15 mm apart,
   wherein each filament of the plurality of second filaments includes a length between two successive attachment sites overlying and in contact with a surface o the mesh facing the sheet,
   wherein the length is fused to the sheet, and
   wherein the interstices at said surface of the mesh proximate to the fused sheet remain unobstructed.

2. A prosthesis according to claim 1, wherein the mesh is made of polypropylene.

3. A prosthesis according to claim 1, wherein the sheet is made of expanded polytetrafluoroethylene.

4. A prosthesis according to claim 1, wherein the plurality of second filaments are the same material as the mesh.

5. A prosthesis according to claim 1, wherein a ratio between a diameter of the second filaments and the mesh filaments is between 1.1 and 2.

6. A prosthesis according to claim 1, wherein the spacing between the plurality of second filaments is less than or equal to 3 mm.

7. A prosthesis according to claim 1, wherein the spacing between the plurality of second filaments is between 1 and 2 mm.

8. A prosthesis according to claim 1, wherein the plurality of second filaments are substantially equally spaced.

9. A prosthesis according to claim 1, wherein the lengths of the second filaments at between two successive attachment sites are less than or equal to 10 mm.

10. A prosthesis according to claim 1, wherein the lengths of the second filaments at between two successive attachment sites are between 5 and 9 mm.

11. A prosthesis according to claim 1, wherein the lengths of the plurality of second filaments are all substantially of the same length, and
   wherein the similar attachment sites of the plurality of second filaments are arranged in rows which are substantially parallel to each other and substantially perpendicular to tie adjacent lengths of the plurality of second filaments.

12. A prosthesis according to claim 1, wherein the prosthesis has a thickness of between 0.4 and 0.6 mm.

13. A prosthesis according to claim 1, wherein the sheet is joined to the lengths through a hot rolling process.

14. A prosthesis according to claim 1, wherein the sheet joining the lengths forms a gap between the sheet and the mesh.

15. The surgical prosthesis of claim 1 wherein the second filaments do not perforate the sheet.

16. A method of repairing soft tissues in a patient following surgical repair of a defective abdominal wall which comprises implanting in the abdominal cavity of a patient a surgical prosthesis as defined by claim 1 using a trocar.

17. The method of claim 16 wherein a wound is formed from treatment of a hernia using an intraperitoneal route.

* * * * *